United States Patent
Hess et al.

(10) Patent No.: US 8,721,529 B2
(45) Date of Patent: May 13, 2014

(54) DEVICES AND METHODS FOR PROVIDING SUCTION AND/OR IRRIGATION IN A SURGICAL PROCEDURE

(75) Inventors: Christopher J. Hess, Cincinnati, OH (US); Duane Linenkugel, Cincinnati, OH (US); David B. Griffith, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 207 days.

(21) Appl. No.: 13/250,123

(22) Filed: Sep. 30, 2011

(65) Prior Publication Data

US 2013/0085337 A1    Apr. 4, 2013

(51) Int. Cl.
*A61B 1/12* (2006.01)

(52) U.S. Cl.
USPC ........... 600/127; 600/129; 600/152; 600/153; 600/156; 600/157; 600/158

(58) Field of Classification Search
USPC ............... 600/127, 129, 152–153, 156–158
See application file for complete search history.

(56) References Cited

U.S. PATENT DOCUMENTS

| | | | | |
|---|---|---|---|---|
| 5,193,525 A | * | 3/1993 | Silverstein et al. | 600/125 |
| 5,352,219 A | | 10/1994 | Reddy | |
| 5,386,817 A | * | 2/1995 | Jones | 600/157 |
| 5,441,059 A | | 8/1995 | Dannan | |
| 5,514,084 A | * | 5/1996 | Fisher | 600/157 |
| 5,518,502 A | * | 5/1996 | Kaplan et al. | 600/157 |
| 5,593,402 A | | 1/1997 | Patrick | |
| 5,630,795 A | * | 5/1997 | Kuramoto et al. | 600/157 |
| 5,989,183 A | * | 11/1999 | Reisdorf et al. | 600/156 |
| 6,010,495 A | | 1/2000 | Tilton, Jr. | |
| 6,059,719 A | * | 5/2000 | Yamamoto et al. | 600/127 |
| 6,409,657 B1 | * | 6/2002 | Kawano | 600/157 |
| 6,962,564 B2 | * | 11/2005 | Hickle | 600/127 |
| 8,047,215 B1 | * | 11/2011 | Sasaki | 600/157 |
| 8,419,624 B2 | * | 4/2013 | James et al. | 600/157 |
| 2002/0173699 A1 | * | 11/2002 | Becker et al. | 600/157 |
| 2011/0087265 A1 | | 4/2011 | Nobis et al. | |
| 2011/0087266 A1 | | 4/2011 | Conlon et al. | |
| 2011/0087267 A1 | | 4/2011 | Spivey et al. | |

FOREIGN PATENT DOCUMENTS

| | | |
|---|---|---|
| WO | 95/19145 A1 | 7/1995 |
| WO | 97/36622 A1 | 10/1997 |
| WO | 02/064192 A1 | 8/2002 |

OTHER PUBLICATIONS

International Search Report an Written Opinion mailed Jan. 30, 2013 for Application No. PCT/US2012/056894 (18 Pages).
U.S. Appl. No. 12/873,845, filed Mar. 2012.
U.S. Appl. No. 12/939,441, filed May 2012.
U.S. Appl. No. 13/249,896, filed Apr. 2013.

* cited by examiner

*Primary Examiner* — Matthew J Kasztejna
*Assistant Examiner* — Kevin G Barry, III
(74) *Attorney, Agent, or Firm* — Nutter McClennen & Fish LLP (57) ABSTRACT

Methods and devices are provided for providing suction and/or irrigation to locations within a body cavity. In general, the methods and devices can allow instruments within a body cavity to be cleaned during a surgical procedure without having to remove the instruments from the body cavity. In one embodiment, an end effector is provided that includes an elongate body having a cleaning base formed thereon. The end effector can be configured as a modular element configured to be removably and replaceably attachable to a distal end of an elongate shaft. The cleaning base can have one or more ports formed through a surface thereof. The cleaning base can be configured to provide suction and/or irrigation through the one or more ports to clean a face of a surgical instrument seated in the cleaning base or in close proximity to the cleaning base.

20 Claims, 8 Drawing Sheets

DEVICES AND METHODS FOR PROVIDING SUCTION AND/OR IRRIGATION IN A SURGICAL PROCEDURE

FIELD

The present invention relates generally to medical devices and procedures, and more particularly to devices and methods for providing suction and/or irrigation in a surgical procedure.

BACKGROUND

Minimally invasive surgical (MIS) instruments are often preferred over traditional open surgical devices due to reduced post-operative recovery time and minimal scarring and exposure to infection. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

In MIS procedures, a scoping device can be used to view, engage, and/or treat tissue in a number of ways to achieve a diagnostic or therapeutic effect. During a surgical procedure, the clarity of the view through a scoping device positioned within a patient's body can be diminished, such as by dragging across tissue walls, accumulating tissue and/or other bodily material, contacting other surgical instruments, etc. The view can become so blurred, distorted, and/or obstructed to the point that the scoping device becomes unusable for visualization and must be withdrawn from the patient's body for replacement with another scoping device or to remove any material that has accumulated on the scoping device before reinserting the scoping device into the body. However, due to difficulty in maneuvering caused by the flexible nature of the scoping device, to obstructions within the body, and/or to the impaired visualization, removal of the scoping device can be inconvenient, cause delays in the surgical procedure, and increase risks, such as contamination and tissue trauma caused by instrument removal and insertion. Upon reinsertion of the scoping device, or insertion of another scoping device, additional time is necessary for the surgeon to reorient the scoping device to a desired location within the body. Furthermore, blurring, distortion, and/or obstruction of a scoping device can occur multiple times throughout a surgical procedure, thereby requiring multiple rounds of scoping device withdrawal from the body prior to the end of the surgical procedure.

Accordingly, there remains a need for devices and methods for cleaning visualization instruments during surgical procedures.

SUMMARY

The present invention generally provides devices and methods for providing suction and/or irrigation in a surgical procedure. In one embodiment, a surgical device is provided that includes a shaft, an end effector, and a cleaning base. The shaft has a proximal end, a distal end, and a lumen extending therethrough. The distal end of the shaft is configured to be positioned within a body cavity. The end effector has a longitudinal body with a distal end, a proximal end, and a lumen extending therein. The proximal end of the end effector is configured to removably and replaceably mate with the distal end of the shaft, and the lumen of the end effector is configured to provide suction and irrigation. The lumen of the shaft is configured to be in fluid communication with the lumen of the end effector when the end effector is mated with the distal end of the shaft such that suction and irrigation can be provided through the lumen of the shaft and the lumen of the end effector. The cleaning base is formed on the longitudinal body and has at least one suction and irrigation port formed therein.

The cleaning base can have a docking face configured to seat a lens of a surgical viewing instrument. The at least one suction and irrigation port of the cleaning base can be configured to clean the lens when the docking face seats the lens. The docking face can be concave. The docking face can be formed on a portion of the end effector that is angularly oriented with respect to a longitudinal axis of the longitudinal body.

The surgical device can also include a reservoir configured to contain an irrigation fluid configured to be delivered through the at least one suction and irrigation port. The reservoir can be coupled to the surgical device at a variety of locations. For example, the end effector can include the reservoir. For another example, the reservoir can be coupled to a proximal portion of the shaft such that the reservoir is configured to be outside the body cavity when the distal end of the shaft is positioned within the body cavity.

The surgical device can vary in any number of ways. The longitudinal body of the cleaning base can be configured to be at least one of rotated and angularly oriented relative to the shaft when the proximal end of the end effector is mated to the distal end of the shaft. In some embodiments, the shaft can have a tissue-penetrating distal tip.

In another embodiment, a surgical device is provided that includes an end effector having a proximal end configured to removably and replaceably mate to a distal end of an elongate shaft, a proximal portion including a lens cleaning system having a docking surface configured to seat a lens of a surgical instrument and to provide a first irrigation fluid to the seated lens through at least one port formed in the docking surface, and a distal portion including a suction/irrigation system configured to deliver a second irrigation fluid through at least one port formed in the distal portion and to provide a suction force through the at least one port formed in the distal portion. The end effector can have a reservoir formed therein configured to contain the first irrigation fluid, and a lumen formed therein configured to receive the second irrigation fluid and the suction force via the elongate shaft when the end effector is mated to the distal end of the elongate shaft. The lens cleaning system can have a longitudinal axis that is angularly oriented with respect to a longitudinal axis of a body of the end effector in the proximal portion of the end effector.

In another aspect, a surgical kit is provided that includes a surgical device, an end effector, a cleaning base, and a surgical viewing instrument. The surgical device includes a proximal handle having an elongate shaft extending distally therefrom. A distal end of the elongate shaft is configured to be positioned within a body cavity. The end effector has a first suction and irrigation port formed therein. A proximal end of the end effector is configured to removably and replaceably mate with a distal end of the elongate shaft. The cleaning base is formed on the end effector and has a docking face with a second suction and irrigation port formed therein. The surgical viewing instrument is configured to be positioned within a body cavity and has a distal end configured to be selectively seated in the docking face such that suction and irrigation can be selectively provided through the second suction and irrigation port to the distal end of the surgical viewing instrument. In some embodiments, the distal end of the surgical viewing instrument can have a diameter less than or equal to a diameter of the docking face.

The elongate shaft can have a lumen extending therethrough that is configured to be in fluid communication with the end effector when the proximal end of the end effector is removably and replaceably mated with the distal end of the elongate shaft such that an irrigation fluid and a suction force can be selectively provided through the lumen to the end effector. The lumen can be configured to selectively provide the irrigation fluid and the suction force to the first suction and irrigation port without providing the irrigation fluid and the suction force to the second suction and irrigation port.

In another aspect, a surgical method is provided that includes removably and replaceably engaging an end effector that is disposed within a body cavity to a distal end of a shaft disposed within a body cavity, placing a lens of a viewing instrument that is disposed within the body cavity in proximity to the end effector that is disposed within the body cavity, and directing a fluid through the end effector onto the lens to clean the lens. The shaft has a proximal end disposed outside of the body cavity and has a lumen extending between the proximal and distal ends. In some embodiments, the method can also include introducing the end effector through a first access port providing access to the body cavity, and introducing the shaft through a second, different access port providing access to the body cavity.

The lens can be placed in proximity to the end effector in a variety of ways. In some embodiments, placing the lens can include positioning the lens within a recessed docking face of the end effector.

The fluid can be directed through the end effector in any number of ways. For example, the fluid can be directed through the end effector by directing the fluid through the shaft to the end effector, or the fluid can be directed through the end effector by delivering the fluid from a reservoir coupled to the end effector and disposed within the body cavity.

BRIEF DESCRIPTION OF DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides devices and methods for providing suction and/or irrigation to locations within a body cavity. In general, the methods and devices can allow instruments within the body cavity to be cleaned during a surgical procedure without having to remove the instruments from the body cavity. In one embodiment, an end effector is provided that includes an elongate body having a cleaning base formed thereon. The end effector can be configured as a modular element configured to be removably and replaceably attachable to a distal end of an elongate shaft. The cleaning base can have one or more ports formed through a surface thereof. The cleaning base can be configured to provide suction and/or irrigation through the one or more ports to clean a face of an instrument seated in the cleaning base or in close proximity to the cleaning base. The suction and/or irrigation can be selectively provided through the one or more ports, with only one of suction and irrigation being provided at a time, with suction and irrigation being alternately provided, or with suction and irrigation being provided simultaneously. After cleaning, the viewing instrument can be removed from the cleaning base and provide visualization via the newly cleaned face. In this way, the viewing instrument can be cleaned during a surgical procedure without removing it from the body cavity. Such cleaning can therefore save time during a surgical procedure, can help prevent degraded visualization, and/or can reduce chances of damaging body tissue by removing an instrument from the body cavity for cleaning and then reinserting the cleaned instrument, or a replacement instrument, into the patient. Instruments can repeatedly become dirty when in use during a surgical procedure, and the methods and devices provided herein can allow for multiple cleanings of the instrument within a body cavity during the surgical procedure.

Figure 1:
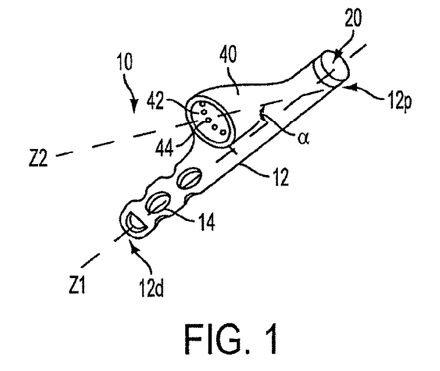
FIG. 1 is a perspective view of one embodiment of a suction and irrigation end effector.

FIG. 1 illustrates one embodiment of an end effector 10 configured to provide suction and/or irrigation such that the end effector 10 can introduce fluid to (e.g., irrigate) and/or remove fluid from (e.g., suction) a targeted location during a surgical procedure. The end effector 10 can have a variety of configurations. As in the illustrated embodiment, the end effector 10 can include an elongate body 12 having a cleaning base 40 extending therefrom at a location between proximal and distal ends 12p, 12d of the body 12.

The proximal end 12p of the body 12 can be configured to removably and replaceably couple the end effector 10 to an elongate shaft of a surgical instrument. To help facilitate mating of the end effector 10 to a substantially cylindrical elongate shaft, a proximal portion of the body 12 can have a substantially cylindrical shape, as shown in the embodiment of FIG. 1. In an exemplary embodiment, the end effector 10 can be configured to be attached to the elongate shaft within a patient's body, e.g., within a body cavity such as the abdominal cavity, and to be removed and replaced within the patient's body. In this way, the elongate shaft can be introduced one time into the patient's body and be used in a variety of different ways, e.g., with a variety of different end effectors, without being removed from the patient's body, which can save time during a surgical procedure and/or reduce tissue trauma. A distal tip of the elongate shaft can have a tissue-penetrating tip, as discussed further below, which can help facilitate passage of the elongate shaft through tissue before the end effector 10 and/or any other end effector is coupled thereto. The end effector 10 can also be configured to be coupled to the elongate shaft outside a patient's body. The body's proximal end 12p can be configured to removably and replaceably couple the end effector 10 to the instrument's elongate shaft using an attachment mechanism, e.g., interference fit, snap fit, threads, etc. Exemplary embodiments of methods and devices for removably and replaceably coupling an end effector to an elongate shaft are described in further detail in U.S. Pat. Pub. No. 2011/0087265 entitled "Laparoscopic Instrument With Attachable End Effector" filed Oct. 9, 2009, U.S. Pat. Pub. No. 2011/0087266 entitled "Loader for Exchanging End Effectors In Vivo" filed Oct. 9, 2009, U.S. Pat. Pub. No. 2011/0087267 entitled "Method for Exchanging End Effectors In Vivo" filed Oct. 9, 2009, U.S. application Ser. No. 12/873,845 entitled "Improved Minimally Invasive Surgery" filed Sep. 1, 2010, U.S. application Ser. No. 13/249,896 entitled "Methods And Devices For Manipulating Tissue In-Vivo" filed on even date herewith, U.S. Pat. No. 5,441,059 entitled "Method of Minimally Invasive Surgery" issued Aug. 15, 1995, and U.S. Pat. No. 5,352,219 entitled "Modular Tools for Laparoscopic Surgery" issued Oct. 4, 1994, which are hereby incorporated by reference in their entireties.

A distal portion of the body 12 can be substantially planar as in the illustrated embodiment, which can help the end effector 10 maneuver through tissue, maneuver between adjacent structures, and/or be positioned against a tissue surface. As in the illustrated embodiment, the distal end 12d of the end effector 10 can be closed and have a blunt or rounded shape, which can help facilitate introduction of the end effector 10 into a body cavity and/or help reduce tissue trauma.

The end effector 10 can be configured to provide suction and/or irrigation in a variety of ways. In one embodiment, the end effector can include one or more areas having a meshed surface, e.g., a surface covered in porous fabric or coated in metal mesh, configured to allow fluid to pass therethrough. In another embodiment, as in the embodiment of FIG. 1, the end effector 10 can include one or more suction and/or irrigation ports formed therein, each of the ports being configured to provide suction and/or irrigation. In an exemplary embodiment, each of the ports can be configured to selectively provide suction and irrigation. However, as will be appreciated by a person skilled in the art, any one of more of the end effector's ports can be dedicated suction ports, and any one of more of the end effector's ports can be dedicated irrigation ports.

The ports can be formed at various locations of the end effector 10. Only one of the elongate body 12 and the cleaning base 40 can include the ports, or, as in the illustrated embodiment, the elongate body 12 can include one or more suction and/or irrigation ports 14 formed therein and the cleaning base 40 can include one or more suction and/or irrigation ports 44 formed therein. In this way, the end effector 10 can provide suction and/or irrigation at a variety of targeted locations. The ports 14 formed through a surface of the elongate body 12, also referred to as "distal ports," and the ports 44 formed through a surface of the cleaning base 40, also referred to as "base ports," can have various configurations, with different ports of the end effector 10 having either the same configurations or varying configurations. The ports 14, 44 can each be in fluid communication with an inner lumen 20 of the end effector 10 and couple with a suction and/or irrigation source therein, as will be appreciated by a person skilled in the art and discussed further below. Although the end effector 10 includes a plurality of suction and/or irrigation ports 14, 44 in the illustrated embodiment, the end effector 10 can include a single suction and/or irrigation port. Similarly, although end effector includes a plurality of distal ports 14 and a plurality of base ports 44, either or both of the body 12 and the base 40 can include a single suction and/or irrigation port. In an exemplary embodiment, the distal ports 14 and the base ports 44 are not in fluid communication with one another such that the distal ports 14 can the base ports 44 can be selectively and separately actuated to provide suction and/or irrigation.

As mentioned above, the distal ports 14 can be located adjacent the distal end 12d of the end effector 10. The distal ports 14 can all have the same size and shape, or, as in the illustrated embodiment, their sizes and shapes can vary. Similarly, the distal ports 14 can have same or different shapes and sizes from the base ports 44. Non-limiting example of port shapes include circular, ovular, square, rectangular, triangular, etc. As in the illustrated embodiment, the distal ports 14 formed on and around the edges of the planar surface of the body's distal portion can be ovular and can occupy a substantial portion of the planar surface. The one of the ports 14 formed closest the rounded distal end 12d of the body 12 can have a semi-circular or half-moon shape, which can help maximize a number of ports 14 formed in the body's distal portion.

Figure 2:
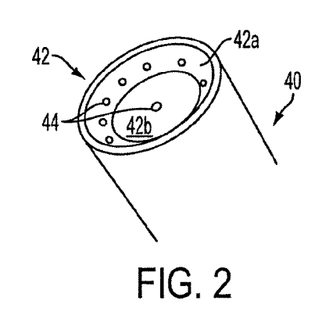
FIG. 2 is an enlarged perspective view of a cleaning base formed on the end effector of FIG. 1.

The cleaning base 40, shown in FIGS. 1 and 2, and its ports 44 can also have a variety of configurations. Generally, the cleaning base 40 can be configured to provide suction and/or irrigation via the base ports 44 to a surgical instrument positioned near a face 42 of the cleaning base 40. The cleaning base 40 can also be configured to seat or dock a surgical instrument to facilitate cleaning of the surgical instrument via the suction and/or irrigation. The cleaning base 40 can have a variety of sizes and shapes. As shown in FIG. 1, the cleaning base 40 can be a substantially cylindrical projection from the elongate body 12. The cleaning base 40 can be angularly oriented with respect to a longitudinal axis Z1 of the elongate body 12. In an exemplary embodiment, the body's longitudinal axis Z1 and the base's longitudinal axis Z2 can be at a non-perpendicular, non-zero angle α, e.g., can be in a range of about 10 to 80 degrees, can be in a range of about 25 to 65 degrees, can be about 45 degrees, can be about 40 degrees, etc. In this way, a surgical instrument can be seated in the base 40 at a non-perpendicular, non-zero angle relative to the body's longitudinal axis Z1, thereby allowing a distal portion of the end effector 10, e.g., the distal portion including the distal ports 14, to be relatively unobstructed such that it can be used at the same time the base 40 cleans the seated instrument. In some embodiments, a distal portion of an end effector having a cleaning base can include a light source such that even when a surgical instrument is docked in the cleaning base, the light source can remain relatively unobstructed so as to provide continuous light to a surgical site.

As mentioned above, the cleaning base 40 can include a face 42, which can have a variety of configurations. The face 42 can be generally distal-facing, as in the illustrated embodiment, which can facilitate approach and seating of a surgical instrument to be cleaned by the base 40. The face 42 can have a variety of sizes and shapes. The size of the face 42 can be slightly larger than a size of a distal end of a surgical instrument to be cleaned to facilitate seating of the distal end of the surgical instrument. For non-limiting example, the face 42 can have a maximum diameter slightly larger than 15 mm to accommodate a 15 mm surgical instrument, the face 42 can have a diameter slightly larger than 3 mm to accommodate a 3 mm surgical instrument, etc. Similarly, the shape of the face 42 can conform to a shape of a distal end of a surgical instrument to be cleaned to facilitate seating of the distal end of the surgical instrument. In some embodiments, the face 42 can be substantially planar, e.g., be a substantially flat distal-most surface of the base 40. As in the illustrated embodiment, the face 42 can be concave, e.g., be formed as a cavity within the base 40, such as in a distal-most end thereof. The face 42 being concave can help facilitate stable seating of a surgical instrument to be cleaned by the base 40. The docking face 42 can optionally have an engagement and/or release feature (not shown), e.g., a textured surface, a releasable clip, configured to facilitate docking and undocking various instruments thereto.

Figure 4:
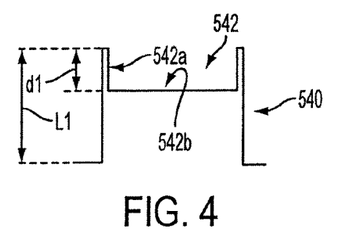
FIG. 4 is a cross-sectional view of one embodiment of a cleaning base of a suction and irrigation end effector with a shallow docking face.
Figure 5:
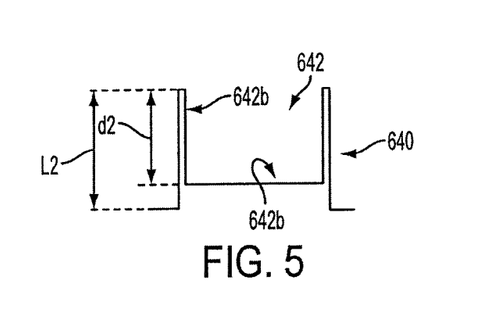
FIG. 5 is a partial cross-sectional view of one embodiment of a cleaning base of a suction and irrigation end effector with a deep docking face.

The face 42 can have a variety of concave shapes, e.g., conical (e.g., right circular, pyramid, frustoconical, etc.), semi-spherical, half-cylindrical, half-cube, etc. The face 42 in the illustrated embodiment, also shown in FIG. 3, has a frustoconical shape and includes a tapered sidewall 42a tapering proximally to a substantially planar bottom 42b. FIGS. 4 and 5 illustrate embodiments of cleaning bases 540, 640 having half-cylindrical faces 542, 642 in which their respective bottoms 542b, 642b are substantially perpendicular to their respective sidewalls 542a, 642a.

Figure 3:
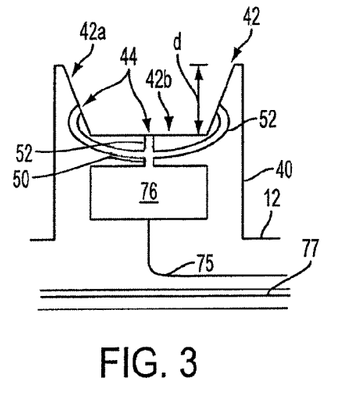
FIG. 3 is a cross-sectional view of the cleaning base of FIG. 2 having a reservoir formed therein.

A depth d of the concave face 42, shown in FIG. 3, can vary. Generally, the greater the depth d, the longer the sidewall 42a and the more enclosed a surgical instrument seated in the base 40, thereby more securely seating the surgical instrument than, e.g., a shallower cavity or a non-concave face. FIG. 4 illustrates a relatively shallow depth d1 of the face 542 in which the sidewall 542 extends along less than half a total length L1 of the base 540. FIG. 5 illustrates a relatively deep depth of the face 642 in which the sidewall 642 extends along a substantial portion of a total length L2 of the base 540.

Referring again to FIGS. 1-3, the base ports 44 can be formed at a variety of locations in the base 40. Generally, the base ports 44 can be formed in the face 42 of the base 42. In some embodiments, only one of the face bottom 42b and the face sidewall 42b can have one or more of the ports 44 formed therein. As in the illustrated embodiment, at least one of the ports 44 can be formed in the bottom 42b and at least one of the ports can be formed on the sidewall 42a. The ports 44 can be arranged in any way on the face bottom 42b and in any way on the sidewall 42a. For non-limiting example, the ports 44 can be arranged on either or both the bottom 42b and the sidewall 42a in a checkerboard pattern, as a perimeter of a shape (e.g., a circle, a square, etc.), etc. In the illustrated embodiment, the bottom 42b includes a single port 44 at a central point of the bottom 42b, and the sidewall 42a has a plurality of the ports 44 arranged around a perimeter or circumference thereof. The plurality of ports 44 arranged around the sidewall 42a can be spaced equidistantly from one another, as shown in FIGS. 1 and 2. By providing at least one of the ports 44 in the face 42, a distal end of a surgical instrument seated in the base 40 and facing the face 42 can be most directly and efficiently cleaned. Such a configuration can be particularly useful if a surgical instrument seated in the base 40 has a lens at a distal end thereof because the port(s) 44 in the face 42 can be targeted at the lens, as discussed further below. By providing at least one of the ports 44 in the cavity wall, sidewalls of a surgical instrument seated in the base 40 can be most directly and efficiently cleaned. Such a configuration can help clean fluid or other material off the surgical instrument that could otherwise fall or drip into unwanted areas of a surgical site and/or in the way of other portions of the instrument.

In some embodiments, a first number of the base ports 44, e.g., half of a total number of the base ports 44, can be configured to provide suction, while a remaining number of the base ports 44 can be configured to provide irrigation. The suction ports 44 and the irrigation ports 44 can be actuated simultaneously such that fluid ejected or released from the irrigation ports 44 can wash a surgical instrument seated in the base 14, and a substantial amount of the fluid and any material washed off the surgical instrument can be suctioned away via the suction ports 44. In some embodiments, in addition or in alternative to some of the base ports 44 providing suction, the distal ports 14 can be configured to provide suction, and the base ports 44 can be configured to provide irrigation. The distal ports' suction and the base ports' irrigation can be provided simultaneously such that fluid ejected or released from the base ports 44 can wash a surgical instrument seated in the base 14, and a substantial amount of the fluid and any material washed off the surgical instrument can be suctioned away via the distal ports 14.

Suction and/or irrigation can be provided through the ports 14, 44 in a variety of ways. Any fluid, e.g., air, water, saline, etc. can be used as a suction fluid or an irrigation fluid. As in the illustrated embodiment, shown in FIG. 3, the end effector 10 can include an on-board fluid source or reservoir 76 configured to contain a fluid (not shown) therein. Although the on-board reservoir 76 is shown as a cavity enclosed entirely within the cleaning base 40, the on-board reservoir 76 can be located elsewhere, such as enclosed entirely within another portion of the end effector 10 or enclosed within portions of both the base 40 and other areas of the end effector 10. Additionally, although only one reservoir is shown in the illustrated embodiment, an end effector can include a plurality of reservoirs. For non-limiting example, the end effector can include at least one suction reservoir configured to receive fluid and/or other material suctioned through one or more ports and at least one irrigation reservoir configured to release fluid through one or more ports for irrigation. For another non-limiting example, the end effector can include multiple reservoirs, each of the reservoirs containing a different irrigation fluid.

The reservoir 76 can be configured as a suction reservoir configured to receive fluid and/or other material suctioned through one or more of the ports 44, the reservoir 76 can be configured as an irrigation reservoir configured to release fluid contained therein through one or more of the ports 44, or the reservoir 76 can be configured as both a suction and irrigation reservoir. In an exemplary embodiment, the reservoir can be configured as an irrigation reservoir, and the end effector can include a separate suction mechanism, e.g., a lumen extending through the base and the end effector to suction fluid therethrough.

A conduit 50 can extend between the reservoir 76 and each of the ports 44 via passages 52 that each correspond to one of the ports 44 and leads directly to its one of the ports 44. The reservoir 76 can be configured to release fluid therefrom and into the conduit 50, and hence into the passages 52 and out the ports 44, via an actuator 75 coupled to the reservoir 76. The actuator 75 can have a variety of configurations, as will be appreciated by a person skilled in the art. In the illustrated embodiment, the actuator 75 includes an electrical wire configured to be actuated external to the end effector 10, e.g., external to a patient in which the end effector 10 is disposed, to stimulate release of the fluid from the reservoir 76.

The reservoir 76 in the illustrated embodiment of FIG. 3 is dedicated to the base ports 44. The end effector 10 can include another reservoir dedicated to the distal ports 14, or the end effector 10 can include a second conduit 77, e.g., within the end effector's inner lumen 20, configured to provide irrigation and/or suction via an external source (not shown). Alternatively, the same reservoir contained with an end effector can be configured to provide irrigation and/or suction to both the distal and base ports 14, 44.

Figure 6:
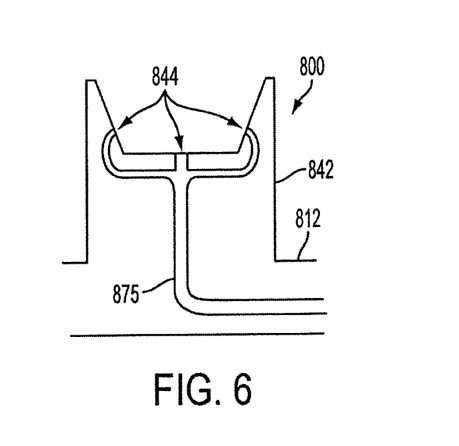
FIG. 6 is a partial cross-sectional view of another embodiment of a cleaning base of a suction and irrigation end effector having a fluid lumen extending therethrough.

FIG. 6 illustrates an embodiment in which suction and/or irrigation is provided from a fluid source located external to an end effector 800. The end effector 800 includes an elongate body, a cleaning base 842 integrally formed with the elongate body 812, and a fluid conduit 875 extending through the elongate body 812 and the base 842. The fluid conduit 875 can be in fluid communication with each of the end effector's ports 844 so as to provide irrigation and/or suction therethrough. The conduit 875 can extend from a source (not shown) located external to the end effector 800, e.g., from a reservoir located at a proximal handle of a device to which the end effector 800 is attached, through a proximal end (not shown) of the body 812, and to each of the ports 844. In this way, if the fluid source becomes empty, clogged, or otherwise needs attention during a surgical procedure, the fluid source can be attended to without removing the end effector 800 from within a patient and/or without moving the end effector 800 positioned with the patient. The external fluid source can be actuated in any number of ways, e.g., push button, releasable clamp, a lever, an electric switch, etc., as will be appreciated by a person skilled in the art.

Figure 7:
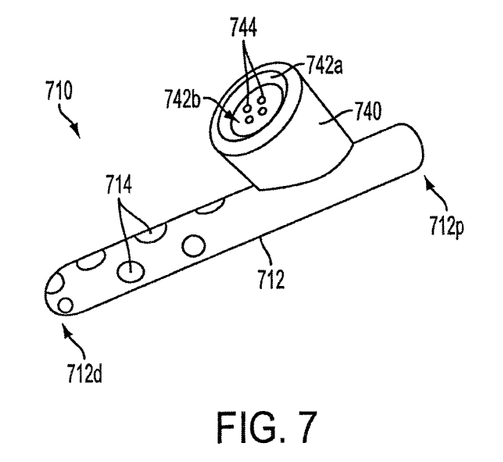
FIG. 7 is perspective view of one embodiment of a suction and irrigation end effector including a removable and replaceable cleaning base.
Figure 8:
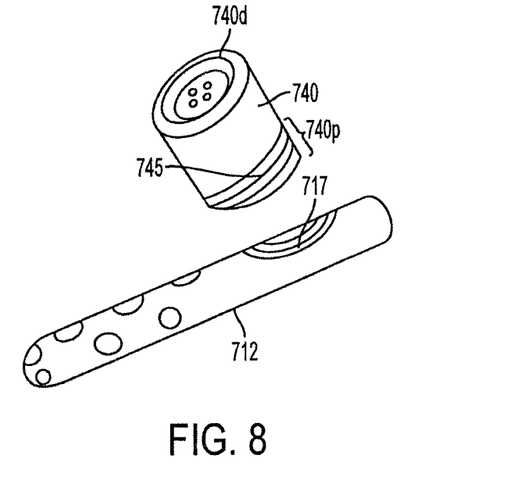
FIG. 8 is an exploded view of the end effector of FIG. 7 showing the cleaning base removed from the end effector.

In the illustrated embodiments of FIG. 1-6, a cleaning base is integrally formed with an elongate body of an end effector. However, in some embodiments, a cleaning base can be configured to be removably and replaceably coupled to an elongate body of an end effector. FIGS. 7 and 8 illustrate one embodiment of a cleaning base 740 configured to removably and replaceably mate to an elongate body 712 of an end effector 710. FIGS. 7 and 8 also show an embodiment in which the elongate body 712 has a substantially cylindrical shape between proximal and distal ends 712p, 712d thereof, in which the body 712 has a plurality of substantially circular distal ports 714 formed therein, and in which a bottom 742b of the base 740 includes ports 744 while a sidewall 742a of the base 740 lacks ports. The ports 744 in this illustrated embodiment are arranged as corners of a square. The base 740 can be configured to couple to the body 712 in a variety of ways, e.g., interference fit, snap fit, threads, etc. In the illustrated embodiment, a proximal portion 740p of the cleaning base 740 has threads 745 formed on an external surface thereof configured to threadably engage a corresponding threads 717 of the elongate body 712. The body's threads 717 can be in a recessed portion of the body 712, as shown in FIG. 8, which can allow the threads 717, 745 to be "hidden" when the base 740 is fully screwed into the body 712 and allow the base 740 and the body 712 to be mated together without an appreciable gap therebetween through which fluid or other material can enter or exit. The embodiment of FIGS. 7 and 8 shows the cleaning base 740 configured to mate to a proximal portion of the elongate body 712, but in other embodiments, the cleaning base 740 can be configured to mate to another portion of the body 712, e.g., a distal portion thereof.

A removable and replaceable end effector such as the end effector 710 of FIGS. 7 and 8 can be configured to include an on-board fluid source or reservoir, e.g., similar to FIG. 3, or it can be configured to couple to an external fluid source or reservoir, e.g., similar to FIG. 4. If the end effector has an on-board reservoir, then the cleaning base and the end effector's body can have corresponding electrical contacts, or other corresponding actuation features, configured to engage when the base is attached to the body to allow actuation of the reservoir. If the end effector couples to an external fluid source, then the cleaning base and the end effector's body can have corresponding conduits configured to align and sealably engage when the base is attached to the body to allow fluid to flow the corresponding conduits.

In some embodiments, a cleaning base can be configured to couple to an elongate body such that the cleaning base can be attached to the body at various angles and/or to be movably attached to the body. For non-limiting example, the base can be configured to snap onto a surface of the body, e.g., via locking male and female connectors, and be slidably moved therealong, e.g., via a slidable track or a toothed rack.

Figure 9:
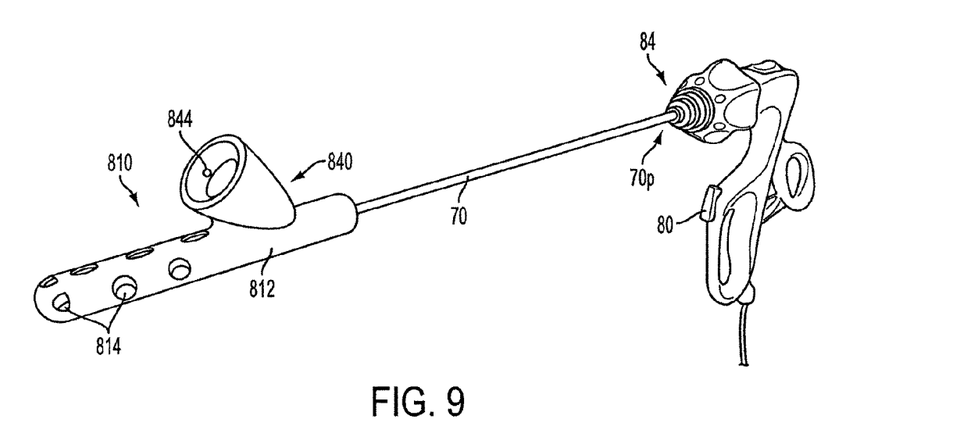
FIG. 9 is a perspective view of another embodiment of a suction and irrigation end effector mated to a distal end of an instrument shaft.
Figure 10:
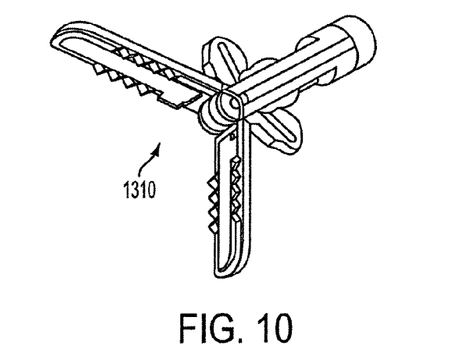
FIG. 10 is a perspective view of one embodiment of a bi-polar forceps end effector.
Figure 11:
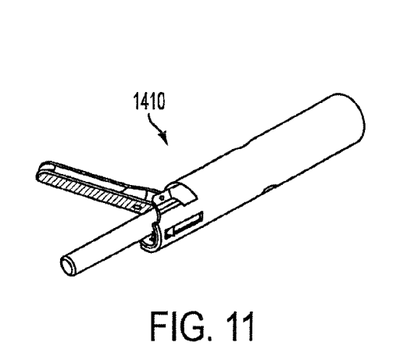
FIG. 11 is a perspective view of one embodiment of an ultrasonic shears end effector.

Any of the suction and/or irrigation end effector described herein can be provided as part of a kit including a surgical instrument including an elongate shaft and, a plurality of end effectors each configured to removably and replaceably mate to a distal end of the surgical instrument's elongate shaft, as discussed above. The kit can include one or more suction and/or irrigation end effectors such as any of those described herein, and/or the kit can include a plurality of end effectors each having a different function from one or more of the other end effectors included with the kit. For non-limiting example, FIGS. 9-11 illustrate various embodiments of end effectors that can be configured to mate to a distal end (obscured in FIG. 9) of an elongate shaft 70 having a handle 84 at a proximal end 70p thereof. FIG. 9 illustrates a suction and/or irrigation end effector 810 attached to the shaft's distal end, FIG. 10 illustrates a bi-polar forceps end effector 1310 configured to attach to the shaft's distal end, and FIG. 11 shows an ultrasonic shears end effector 1410 configured to attach to the shaft's distal end. The end effector 810 of FIG. 9 is similar to the end effector 710 of FIG. 7 except that the end effector 810 of FIG. 9 has an integrally formed cleaning base 840 and elongate body 812. FIG. 9 also illustrates an actuation button 80 formed on the handle 84 that can be depressed to provide suction and/or irrigation through ports 814, 844 of the end effector 810. When the button 80 is released, suction and/or irrigation can cease being provided through the ports 814, 844. A person skilled in the art will appreciate that mechanisms other than the button 80, e.g., a lever, a switch, etc., can be used to actuate the end effector's suction and/or irrigation functions.

The bi-polar forceps end effector 1310 and the ultrasonic shears end effector 1410, as well as exemplary embodiments of other removable and replaceable end effectors and exemplary embodiments of methods and devices for attaching and using end effectors to shafts, are described in further detail in previously mentioned U.S. Pat. Pub. No. 2011/0087265 entitled "Laparoscopic Instrument With Attachable End Effector" filed Oct. 9, 2009, U.S. Pat. Pub. No. 2011/0087266 entitled "Loader for Exchanging End Effectors In Vivo" filed Oct. 9, 2009, U.S. Pat. Pub. No. 2011/0087267 entitled "Method for Exchanging End Effectors In Vivo" filed Oct. 9, 2009, U.S. application Ser. No. 12/873,845 entitled "Improved Minimally Invasive Surgery" filed Sep. 1, 2010, U.S. application Ser. No. 13/249,896 entitled "Methods And Devices For Manipulating Tissue In-Vivo" filed on even date herewith, U.S. Pat. No. 5,441,059 entitled "Method of Minimally Invasive Surgery" issued Aug. 15, 1995, and U.S. Pat. No. 5,352,219 entitled "Modular Tools for Laparoscopic Surgery" issued Oct. 4, 1994.

In use, a suction and irrigation end effector can be mated to a distal end of an instrument shaft via a proximal end of its elongate body. As mentioned above, the end effector can either be mated outside a patient's body, e.g., ex vivo prior to introduction of the distal end of the instrument shaft into a patient's body cavity, or alternatively, the end effector can be mated to the shaft within the patient's body, e.g., in vivo within the patient's body cavity.

Figure 12:
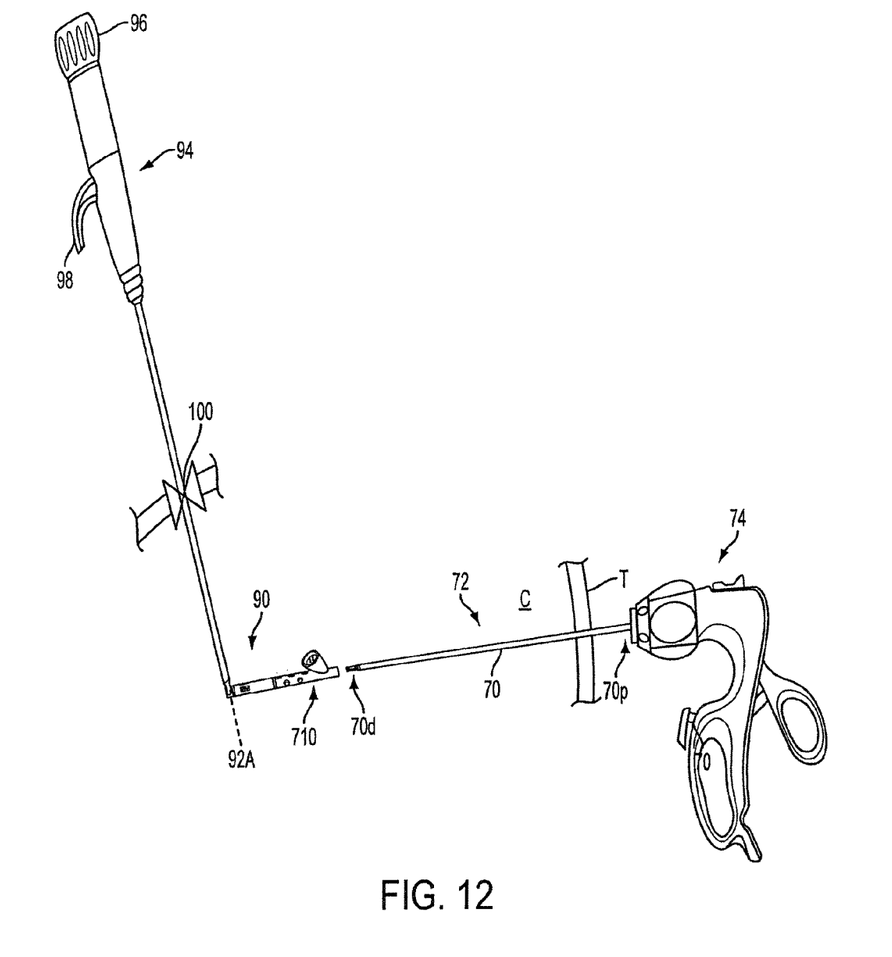
FIG. 12 is a perspective view of another embodiment of an end effector being placed in position to couple to a distal end of an instrument shaft.
Figure 13:
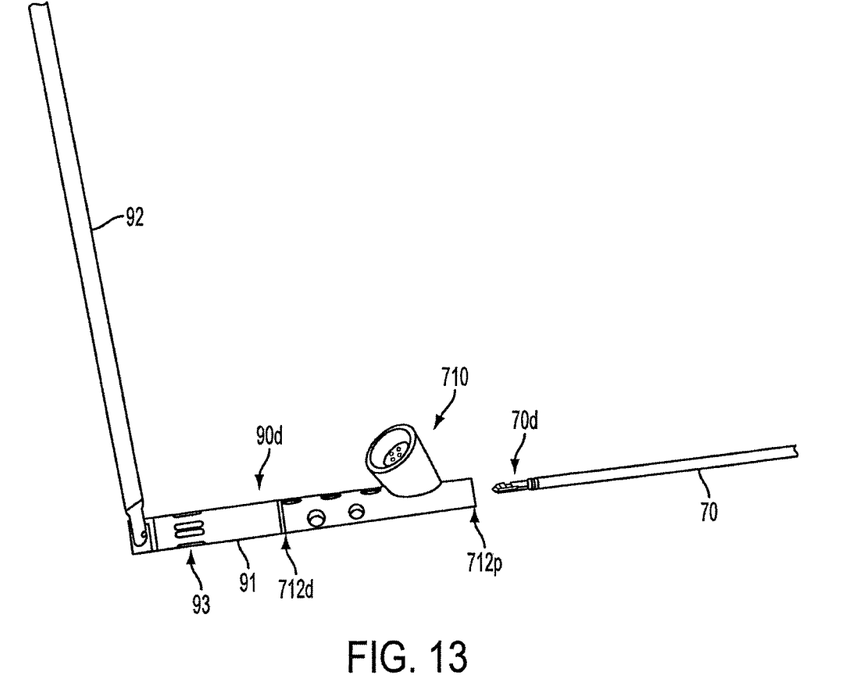
FIG. 13 is an enlarged perspective view of the end effector and the distal end of the instrument shaft of FIG. 12.
Figure 14:
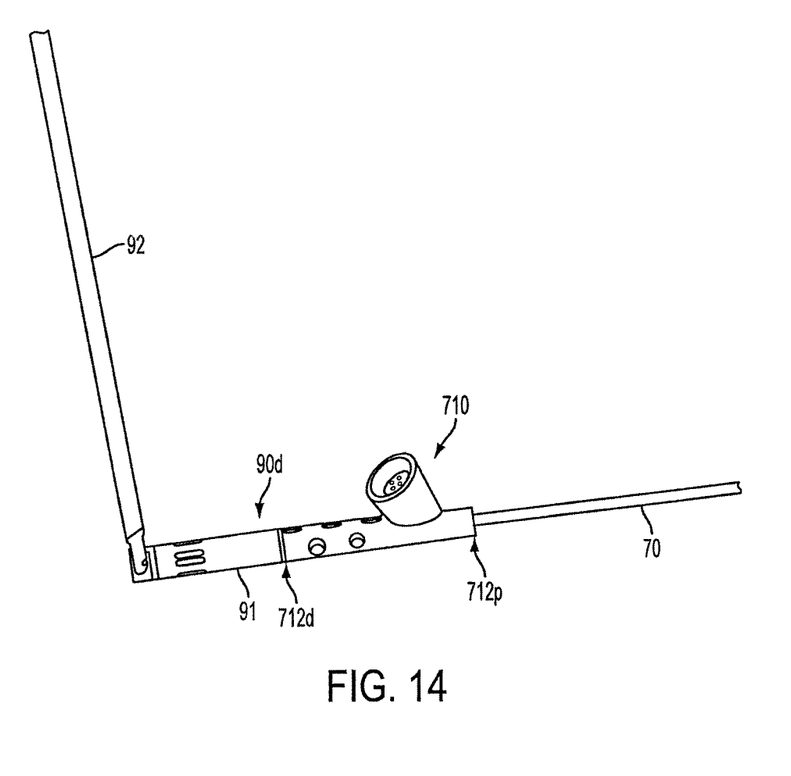
FIG. 14 is a perspective view of the end effector of FIG. 12 coupled to the distal end of the instrument shaft of FIG. 12.

FIGS. 12-14 illustrate an exemplary embodiment of attaching the end effector 710 of FIG. 7 to a distal end 70d of an elongate shaft 70 configured to be positioned within a body cavity C. Although FIGS. 12-14 illustrate the end effector 710 of FIG. 7 being attached to the shaft 70, as mentioned above, other end effectors can be attached to the shaft 70 in a similar way. Further, although FIGS. 12-14 illustrate the end effector 710 of FIG. 7 being attached to the shaft 70 within the body cavity C, as mentioned above, the end effector 710 (or any other end effector) can be attached to the shaft 70 exterior to the body cavity C, e.g., before the shaft 70 passes through a tissue wall T. As shown in FIG. 12, the distal end 70d of the instrument shaft 70 can include a tissue-penetrating tip configured to pierce through the tissue wall T and directly enter the body cavity C. A person skilled in the art will appreciate that a small incision or other mark can be made on an exterior surface of the tissue wall T prior to advancement of the distal end 70d therethrough to help facilitate the advancement. A person skilled in the art will also appreciate that instead of being advanced into the body cavity C directly through an opening formed in the tissue wall T, the shaft 70 can be advanced into the body cavity C in another way, such as translumenally, e.g., transorally, or through a trocar passed through the tissue wall T.

The end effector 710 can be loaded ex vivo into a distal end 90d of an elongate shaft 92 of a loader device 90. The distal end 90d with the end effector 710 coupled thereto can then be introduced into the body cavity through a tissue opening 100, as shown in FIGS. 12 and 13, with the shaft 92 positioned within the opening 92. The loader 90 can hold the end effector 710 during in vivo attachment to and in vivo detachment from the shaft 70 of an instrument 72. The loader 90 and the instrument 72 can each includes respective proximal handles 94, 74 attached to the proximal ends of their respective shafts 92, 70. The handles 94, 74 can be configured to be positioned ex vivo, as shown in FIG. 12, to facilitate user handling of the loader 90 and the instrument 72 when distal ends of the devices 90, 72 are positioned within a patient. The same user can handle both of the loader 90 and the instrument 72, or they can be handled by different user.

Generally, the loader 90 can be configured to facilitate introduction of the end effector 710 into the body cavity 710 and coupling of the end effector 710 to the shaft 70 within the body cavity C. The loader shaft 92 in this illustrated embodiment is rigid and straight, but the shaft 92 can be curved or flexible, which can be beneficial for natural orifice transluminal introduction of the distal end 90d to a surgical field. The loader 90 can include a movable distal end 90d, as shown in the illustrated embodiment. The distal end 90d can be configured to be movable in a variety of ways, such as angularly and rotationally. A knob 96 at the loader handle 94 can be configured to selectively rotate about a longitudinal axis 92A of the shaft 92 to angularly articulate the distal end 90d relative to the shaft's longitudinal axis 92A. The distal end 90d can be introduced and removed through the opening 100 in-line with the shaft 92, and then be articulated in vivo to facilitate alignment between the end effector 710 and the distal end 70d of the shaft 70. The loader handle 94 can include an arm 98 configured to facilitate grasping of the handle 94 and rotational orientation of the articulated distal end 90d about the shaft axis 92A. As in the illustrated embodiment, the arm 98 can be rigidly connected the handle 94.

As in this illustrated embodiment, the distal end 90d of the loader 90 can include a tube opening at its distal tip. The tube 91 can be dimensioned to receive the distal end 712d of the end effector's body. The tube 91 can include an engagement feature 93 for holding the end effector 710. While the engagement feature 93 can have a variety of configurations, as in this illustrated embodiment a plurality of leaf springs can provide an interference fit with the end effector 710 to frictionally hold the end effector 710 in the tube 91. As in this illustrated embodiment, when the end effector 710 is loaded in the tube 91, the end effector body's distal end 712d can be positioned in the tube 91, and the proximal end 712p can extend from the tube 91. This arrangement can help prevent the distal ports 14 from suctioning or irrigating during insertion. Similarly, this arrangement can prevent actuation of distal ends of other end effectors during insertion into a body cavity or during attachment to an instrument shaft, e.g., prevent jaws of an end effector from opening. After the distal end 70d of the instrument 72 is attached to the proximal end 712p of the end effector's body 712, the end effector 710 can be pulled from the distal end 90d of the loader 90.

Because the loader 90 can introduce the end effector 710 into the body cavity C independent of the device 72 to which the end effector 710 can be attached at the distal end 70d thereof, the loader 90 can be repeatedly advanced into and removed from the body cavity C to remove and introduce multiple end effectors into the body cavity C for attachment to the shaft 70 without the shaft 70 having to be removed from the body cavity C. For non-limiting example, a suction and/or irrigation end effector such as the end effector 710 of FIGS. 12-14 can be attached to the shaft 70 and remain attached thereto without being replaced by another end effector during the surgical procedure. For another non-limiting example, the loader 90 can be used to attach a first end effector to the shaft 70, and then if another device (not shown) within the body cavity C needs to be cleaned, the loader 90 can be used to remove the first end effector from the shaft 70 and to attach the suction and/or irrigation end effector 710 thereto. The other device can then be docked at the end effector's cleaning base 740, cleaned, and de-docked. The loader 90 can then be used to detach the end effector 710 from the shaft 70 and to attach the first end effector or another end effector to the shaft 70.

Figure 15:
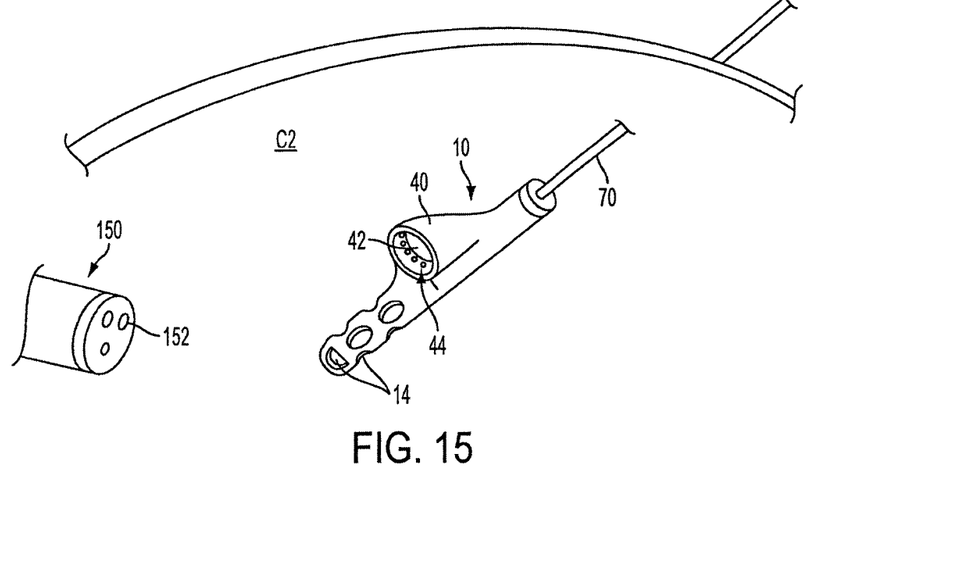
FIG. 15 is a perspective view of the suction and irrigation end effector of FIG. 1 positioned within a body cavity and of one embodiment of a viewing instrument positioned within the body cavity, the end effector being coupled to a distal end of an instrument shaft inserted through a tissue wall and into the body cavity.
Figure 16:
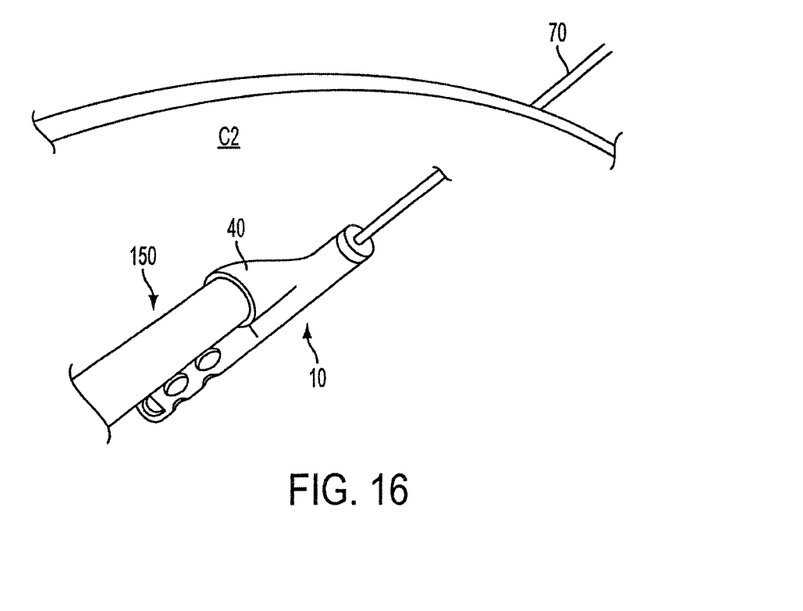
FIG. 16 is a perspective view of the suction and irrigation end effector and the instrument shaft of FIG. 15 with a distal end of the viewing instrument seated in a cleaning base of the end effector within the body cavity.
Figure 17:
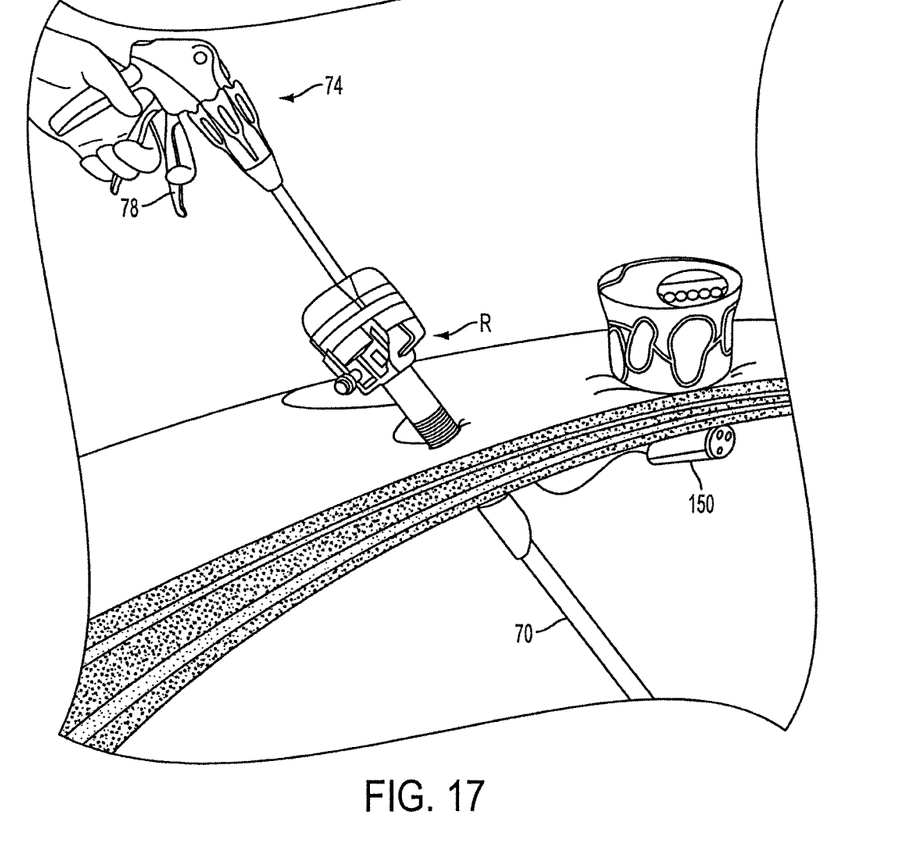
FIG. 17 is a perspective view of the instrument shaft of FIG. 12 inserted into a body cavity through a trocar and another embodiment of a viewing instrument disposed within the body cavity.

FIGS. 15 and 16 illustrate the suction and/or irrigation end effector 10 of FIG. 1 attached to the shaft 70 of the device 72 of FIG. 12. The end effector 10 coupled to the shaft 70 can be positioned within a body cavity C2. A viewing instrument, e.g., a magnetically controlled camera 150, also shown in FIG. 17, can also be positioned within the body cavity C2. If a viewing lens 152 at a distal end of the camera 150 becomes smeared, obstructed with debris stuck thereto, or otherwise dirtied, the distal end of the scoping device 150 can be seated in the cleaning base 40, as shown in FIG. 16. The distal end including the lens 152 can then be cleaned via the base ports 44 and optionally also the distal ports 14, and then the camera 150 can be de-docked from the base 40. Exemplary embodiments of a magnetically controlled camera devices and methods are described in further detail in U.S. application Ser. No. 12/939,441 entitled "Light-Based, Transcutaneous Video Signal Transmission" filed Nov. 4, 2010, U.S. application Ser. No. 12/873,845 entitled "Improved Minimally Invasive Surgery" filed Sep. 1, 2010, and U.S. application Ser. No. 13/249,896 entitled "Methods And Devices For Manipulating Tissue In-Vivo" filed on even date herewith, which are hereby incorporated by reference in their entireties. Although the illustrated camera is a magnetically controlled camera 150 in the illustrated embodiment of FIGS. 15-17, any type of instrument, such as a viewing instrument, e.g., a scoping device having a distal lens, can be configured to be seated in and cleaned by a suction and/or irrigation end effector such as the end effector 10 shown in FIGS. 15-17. Non-limiting examples of a scoping device include an endoscope, a laparoscope, a gastroscope, and a colonoscope. Also, although the shaft 70 is shown inserted through a trocar R in the embodiment of FIG. 17, as mentioned above, the shaft 70 can be introduced into a patient in any number of other ways. FIG. 17 also illustrates an actuator in the form of a trigger 78 coupled to the handle 74 of the device 72 that can be configured to be actuated, e.g., pulled to cause suction and/or irrigation at the end effector 10 (not shown in FIG. 17).

As mentioned above, the cleaning base of an end effector can be configured to clean a surgical instrument positioned near the base but not necessarily seated therein. For non-limiting example, if a diameter of a distal end of a camera is larger than a diameter of the base such that the camera's distal end cannot be seated therein, the camera's distal end could be positioned near the base. The base ports and/or the distal ports can then provide suction and/or irrigation in a general direction of the nearby camera's distal end to clean the camera's distal end. In this way, the end effector can be configured to clean a variety of different instruments during the same surgical procedure. For another non-limiting example, if a portion of a surgical device to be cleaned cannot be oriented to be seated in the cleaning base, e.g., because an elongate shaft of a device is too short for its distal end to reach the base, then the portion of the surgical device to be cleaned can be positioned near the base and cleaned without being seated in the base. For yet another non-limiting example, if a portion of a surgical device to be cleaned has a shape incompatible with a shape of the cleaning base's face such that the portion of the surgical device to be cleaned cannot be seated in the base, then the portion of the surgical device to be cleaned can be positioned near the base and cleaned in that position proximate to the base.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
 a shaft having a proximal end, a distal end, and a lumen extending therethrough, the distal end being configured to be positioned within a body cavity;
 an end effector having a longitudinal body with a distal end, a proximal end, and a lumen extending therein, the proximal end of the end effector being configured to removably and replaceably mate with the distal end of the shaft, and the lumen of the end effector being configured to provide suction and irrigation, the lumen of the shaft being configured to be in fluid communication with the lumen of the end effector when the end effector is mated with the distal end of the shaft such that suction and irrigation can be provided through the lumen of the shaft and the lumen of the end effector; and
 a cleaning base formed on the longitudinal body and having at least one suction and irrigation port formed therein, a distal end of the cleaning base being proximal to the distal end of the end effector.

2. The device of claim 1, wherein the cleaning base has a docking face configured to seat a lens of a surgical viewing instrument, the at least one suction and irrigation port of the cleaning base being configured to clean the lens when the docking face seats the lens.

3. The device of claim 2, wherein the docking face is concave.

4. The device of claim 2, wherein the docking face is formed on a portion of the end effector that is angularly oriented with respect to a longitudinal axis of the longitudinal body.

5. The device of claim 1, further comprising a reservoir configured to contain an irrigation fluid configured to be delivered through the at least one suction and irrigation port.

6. The device of claim 5, wherein the end effector includes the reservoir.

7. The device of claim 5, wherein the reservoir is coupled to a proximal portion of the shaft such that the reservoir is configured to be outside the body cavity when the distal end of the shaft is positioned within the body cavity.

8. The device of claim 1, wherein the longitudinal body of the end effector is configured to be at least one of rotated and angularly oriented relative to the shaft when the proximal end of the end effector is mated to the distal end of the shaft.

9. The device of claim 1, wherein the shaft has a tissue-penetrating distal tip.

10. The device of claim 1, wherein the cleaning base has a cavity formed therein that is configured to seat a portion of a surgical instrument therein, the at least one suction and irrigation port being configured to selectively provide suction and irrigation to the portion of the surgical instrument seated in the cavity.

11. The device of claim 2, wherein the docking face is at a distal-most end of the cleaning base.

12. The device of claim 1, wherein a longitudinal axis of the cleaning base is different offset from a longitudinal axis of the longitudinal body.

13. The device of claim 1, wherein the cleaning base extends from the longitudinal body at a non-perpendicular, non-zero angle with respect to a longitudinal axis of the longitudinal body.

14. A surgical kit, comprising:
a surgical device including a proximal handle having an elongate shaft extending distally therefrom, a distal end of the elongate shaft being configured to be positioned within a body cavity;
an end effector having a first suction and irrigation port formed therein, a proximal end of the end effector being configured to removably and replaceably mate with the distal end of the elongate shaft;
a cleaning base formed on the end effector, the cleaning base having a recessed docking face on an exterior surface thereof, the docking face having a second suction and irrigation port formed therein; and
a surgical viewing instrument configured to be positioned within a body cavity and having a distal end configured to be selectively seated within the recessed docking face such that suction and irrigation can be selectively provided through the second suction and irrigation port to the distal end of the surgical viewing instrument.

15. The kit of claim 14, wherein the elongate shaft has a lumen extending therethrough that is configured to be in fluid communication with the end effector when the proximal end of the end effector is removably and replaceably mated with the distal end of the elongate shaft such that an irrigation fluid and a suction force can be selectively provided through the lumen to the end effector.

16. The kit of claim 15, wherein the lumen is configured to selectively provide the irrigation fluid and the suction force to the first suction and irrigation port without providing the irrigation fluid and the suction force to the second suction and irrigation port.

17. The kit of claim 14, wherein the distal end of the surgical viewing instrument has a diameter less than or equal to a diameter of the docking face.

18. The kit of claim 14, wherein the second suction and irrigation port comprises a plurality of suction and irrigation ports.

19. The kit of claim 18, wherein the plurality of suction and irrigation ports are arranged around a perimeter of the docking face.

20. The kit of claim 14, wherein the first suction and irrigation port is distal to the second suction and irrigation port.

* * * * *